US011607160B2

(12) United States Patent
Cuestas Rodriguez (10) Patent No.: US 11,607,160 B2
(45) Date of Patent: Mar. 21, 2023

(54) SYSTEM AND METHOD FOR MULTI MODAL DECEPTION TEST SCORED BY MACHINE LEARNING

(71) Applicant: Carlos Andres Cuestas Rodriguez, Bogota (CO)

(72) Inventor: Carlos Andres Cuestas Rodriguez, Bogota (CO)

(*) Notice: Subject to any disclaimer, the term of this patent is extended or adjusted under 35 U.S.C. 154(b) by 218 days.

(21) Appl. No.: 16/703,703

(22) Filed: Dec. 4, 2019

(65) Prior Publication Data
US 2020/0383621 A1 Dec. 10, 2020

(30) Foreign Application Priority Data

Jun. 5, 2019 (CO) .......................... NC2019/0005899

(51) Int. Cl.
  *A61B 5/16* (2006.01)
  *G06N 20/00* (2019.01)
  (Continued)

(52) U.S. Cl.
  CPC ............ *A61B 5/164* (2013.01); *A61B 5/0077* (2013.01); *A61B 5/015* (2013.01);
  (Continued)

(58) Field of Classification Search
  CPC ............ A61B 5/163; A61B 5/164; A61B 5/11
  See application file for complete search history.

(56) References Cited

U.S. PATENT DOCUMENTS

| | | | | |
|---|---|---|---|---|
| 5,150,969 A | * | 9/1992 | Goldberg | ................. G01J 5/02 |
| | | | | 374/128 |
| 5,771,261 A | * | 6/1998 | Anbar | ..................... A61B 5/01 |
| | | | | 374/45 |

(Continued)

FOREIGN PATENT DOCUMENTS

| | | |
|---|---|---|
| CN | 105105738 A | 2/2015 |
| CN | 104644187 A | 5/2015 |

(Continued)

OTHER PUBLICATIONS

Randal S., O., William, L., Zairah, M., Akshay, V. and Jason H., M., 2018. Data-driven advice for applying machine learning to bioinformatics problems. Biocomputing, 2018, pp. 192-203 (Year: 2018).*

(Continued)

*Primary Examiner* — Lynsey C Eiseman
*Assistant Examiner* — Amanda L Steinberg
(74) *Attorney, Agent, or Firm* — The Morales Law Firm; Joseph L. Morales, Esq.

(57) ABSTRACT

Systems and methods for measuring physiological responses caused by cognitive load and stress to calculate a probability of deception. The system comprises modules to determine changes in pupil dilation, flicker frequency, pupil eye trajectory, face temperature, respiratory rate, position of the user's facial points, heart rate, skin conductivity, body movements, arm temperature, temperature, and electroencephalography signals; and modules to provide stimuli to the user, record conscious responses from the user, receive physiological signals, and determine changes in the user's physiological variables associated with stress and cognitive load in response to the stimuli generated, to calculate a likelihood of deception in conscious responses.

15 Claims, 4 Drawing Sheets

(51) Int. Cl.
*A61B 5/01* (2006.01)
*A61B 5/00* (2006.01)
*A61B 5/0205* (2006.01)
*A61B 5/11* (2006.01)
*A61B 5/377* (2021.01)
*A61B 5/0533* (2021.01)
*A61B 5/024* (2006.01)
*A61B 5/08* (2006.01)

(52) U.S. Cl.
CPC ............ *A61B 5/02055* (2013.01); *A61B 5/11* (2013.01); *A61B 5/163* (2017.08); *A61B 5/377* (2021.01); *A61B 5/7435* (2013.01); *G06N 20/00* (2019.01); *A61B 5/02405* (2013.01); *A61B 5/02416* (2013.01); *A61B 5/0533* (2013.01); *A61B 5/0816* (2013.01)

(56) References Cited

U.S. PATENT DOCUMENTS

| | | | |
|---|---|---|---|
| 7,027,621 | B1 | 4/2006 | Prokoski |
| 7,111,980 | B2 | 9/2006 | Pavlidis et al. |
| 7,138,905 | B2 | 11/2006 | Pavlidis et al. |
| 7,729,755 | B2 | 6/2010 | Laken |
| 8,512,240 | B1 * | 8/2013 | Zuckerman-Stark ........................ G16H 50/30 128/924 |
| 10,113,913 | B2 | 10/2018 | Tzvieli et al. |
| 10,159,411 | B2 | 12/2018 | Tzvieli et al. |
| 10,248,804 | B2 | 4/2019 | Valacich et al. |
| 2003/0032870 | A1 | 2/2003 | Farwell |
| 2003/0120140 | A1 | 6/2003 | Bango, Jr. |
| 2004/0143170 | A1 | 7/2004 | DuRousseau |
| 2008/0260212 | A1 | 10/2008 | Moskal et al. |
| 2010/0324454 | A1 | 12/2010 | Kircher et al. |
| 2014/0371549 | A1 | 12/2014 | Yaffe-Ermoza et al. |
| 2016/0354024 | A1 | 12/2016 | Keshava et al. |
| 2017/0039045 | A1 * | 2/2017 | Abrahami .............. A61B 5/486 |
| 2017/0119296 | A1 | 5/2017 | Macknik et al. |
| 2017/0231490 | A1 | 8/2017 | Toth et al. |
| 2018/0160959 | A1 | 6/2018 | Wilde et al. |
| 2018/0303397 | A1 * | 10/2018 | Krupat ................. A61B 5/4842 |
| 2018/0365784 | A1 * | 12/2018 | Sartori ................... G06Q 50/26 |
| 2019/0251702 | A1 * | 8/2019 | Chandler ................ G06N 3/08 |
| 2019/0384392 | A1 * | 12/2019 | Aimone ................. G06F 3/015 |
| 2020/0138337 | A1 * | 5/2020 | Choi .................... A61B 5/0077 |
| 2020/0390328 | A1 * | 12/2020 | Toth ........................ A61F 7/007 |
| 2021/0212595 | A1 * | 7/2021 | Mills ........................ A61B 5/01 |

FOREIGN PATENT DOCUMENTS

| | | |
|---|---|---|
| CN | 106667506 A | 5/2017 |
| CN | 107280692 A | 10/2017 |
| CN | 107669282 A | 2/2018 |
| WO | 2017136929 A1 | 8/2017 |

OTHER PUBLICATIONS

Agrigoroaie R., Tapus A. (2017) Contactless Physiological Data Analysis for User Quality of Life Improving by Using a Humanoid Social Robot. In: Battiato S., Gallo G., Schettini R., Stanco F. (eds) Image Analysis and Processing—ICIAP 2017. ICIAP 2017. Lecture Notes in Computer Science, vol. 10485. Springer, Cham.

Rajoub, Bashar & Zwiggelaar, Reyer. (2014). Thermal Facial Analysis for Deception Detection. Information Forensics and Security, IEEE Transactions on. 9. 1015-1023. 10.1109/TIFS 2014 2317309.

Weinberger, S. (2010). Airport security: Intent to deceive? Nature(465), 412-415. doi:10.1038/465412a.

M. Abouelenien, V. Pérez-Rosas, R. Mihalcea and M. Burzo, "Detecting Deceptive Behavior via Integration of Discriminative Features From Multiple Modalities," in IEEE Transactions on Information Forensics and Security, vol. 12, No. 5, pp. 1042-1055, May 2017. doi: 10.1109/TIFS.2016.2639344.

Bedoya-Echeverry, Sebastián, Belalcázar-Ramírez, Hernán, Loaiza-Correa, Humberto, Nope-Rodríguez, Sandra Esperanza, Pinedo-Jaramillo, Carlos Rafael, & Restrepo-Girón, Andrés David. (2017). Detection of lies by Facial thermal imagery analysis. Revista Facultad de Ingeniería, 26(44), 47-59. https://dx.doi.org/10.19053/01211129.v26.n44.2017.5771.

* cited by examiner

SYSTEM AND METHOD FOR MULTI MODAL DECEPTION TEST SCORED BY MACHINE LEARNING

CROSS REFERENCE TO RELATED APPLICATIONS

This application claims priority from Colombian application serial number NC2019/0005899 filed on Jun. 5, 2019, which is incorporated herein by reference in its entirety.

FIELD OF THE INVENTION

The present invention relates to systems and methods for measuring physiological responses caused by cognitive load and stress to calculate a probability of deceit.

BACKGROUND OF THE INVENTION

Deception testing systems are widely used in security procedures by government entities, the military or private companies. The goal of the systems is to establish whether the system user is answering in a deceptive or honest way to questions asked.

Common cheating test systems usually monitor skin conductivity, heart rate and respiratory rate. Different developments focus on integrating a few additional variables to improve the success rate. However, many current developments focus on remote systems that do not require direct contact with the user, such as infrared cameras, in order to improve user comfort and the speed at which questions can be asked.

Other current systems usually focus solely on a single technology and do not integrate modules to efficiently and portably measure different physiological variables. In addition, no machine learning algorithms have been developed in depth and applied to deception testing systems that allow comparison and detection of patterns within a large number of physiological variables quickly and effectively. Additionally, it has been shown that there are trainings or methodologies that can circumvent classic deception detection systems based on monitoring a limited number of variables, which decreases their accuracy.

There is a need in the art, then, for a system that efficiently and portably integrates different modules to measure a plurality of physiological variables and relates them to stimulus responses, using machine-learning algorithms to obtain better precision in calculating the probability of deception from responses to stimuli.

BRIEF DESCRIPTION OF THE INVENTION

The present invention solves the precision problems of conventional systems. It refers to physiological response measurement systems caused by cognitive load and stress, and comprises an ocular measurement module containing a video camera and infrared LEDs oriented towards the user's pupils. The module is configured to determine changes in pupil dilation, flicker frequency, and the pupil's eye trajectory. Additionally, it comprises a thermal measurement module with an infrared camera arranged to measure temperature changes in the user's face and respiratory rate, and a facial measurement module with a camera that detects changes in the user's facial position points.

It also comprises a sensor module with heart rate sensors, skin conductivity sensors, motion sensors, and temperature sensors and an electroencephalography (EEG) signal module. The system additionally comprises an interaction and information presentation module, configured to provide a stimulus to the user and record a conscious response from him or her; and an integration and processing module configured to receive signals from the ocular measurement, thermal measurement, facial measurement, sensor, and the EEG electroencephalography signal modules.

The system is set up to determine changes in the user's physiological variables associated with stress and cognitive load in response to the stimulus generated by the interaction and information presentation module, to calculate a probability of deceit in conscious responses.

Another aspect of the invention relates to methods of measuring physiological responses caused by cognitive load and stress. These methods include the following steps: providing stimuli to the user in an interaction and presentation of information module, where the stimuli can be visual text type, image type without text, auditory type or combinations thereof; measuring changes in a user's face temperature and respiratory rate by means of an infrared camera; measuring eye movement, flickering frequency and changes in pupil dilation through a video camera; measuring changes in the position of the user's facial points by means of a second video camera; measuring skin temperature, heart rate, heart rate variation, changes in skin conductivity and movements of the user's hand through a sensor module in direct contact with the skin; measuring changes in electroencephalography electrode (EEG) information; correlating the physiological information obtained in the previous steps with the different types of stimuli provided, and determining the user's level of cognitive load and stress in response to the different types of stimulus, to calculate a probability of deception in conscious responses.

DETAILED DESCRIPTION OF THE INVENTION

The present invention relates to systems for measuring physiological responses 100 caused by cognitive load and stress, comprising an ocular measurement module 110 containing a video camera and infrared LEDs oriented towards the user's pupils 101, configured to determine changes in dilation of the pupils, determine the frequency of blinking and determine the ocular trajectory of the pupils. Additionally, it comprises a thermal measurement module 120 that contains an infrared camera arranged to measure changes in temperature in the user's face and changes in his or her respiratory rate 101, and a facial measurement module 130 containing a camera that detects the user's facial points 101.

It also comprises a sensor module 140 with sensors that can be heart rate sensors, skin conductivity sensors, motion sensors, and temperature sensors, and an electroencephalography (EEG) signal module 150. The system additionally comprises an interaction and presentation of information module 160 configured to provide a stimulus to the user and record a conscious response from the user, and an integration and processing module 170 configured to receive the signals of the ocular measurement module 110, the thermal measurement module 120, the facial measurement module 130, the sensor module 140 and the EEG signal module 150.

The system is configured to determine changes in the user's physiological variables associated with stress and cognitive load, in response to the stimulus generated by the interaction and information presentation module 160, to calculate a probability of deception in conscious responses.

Figure 1:
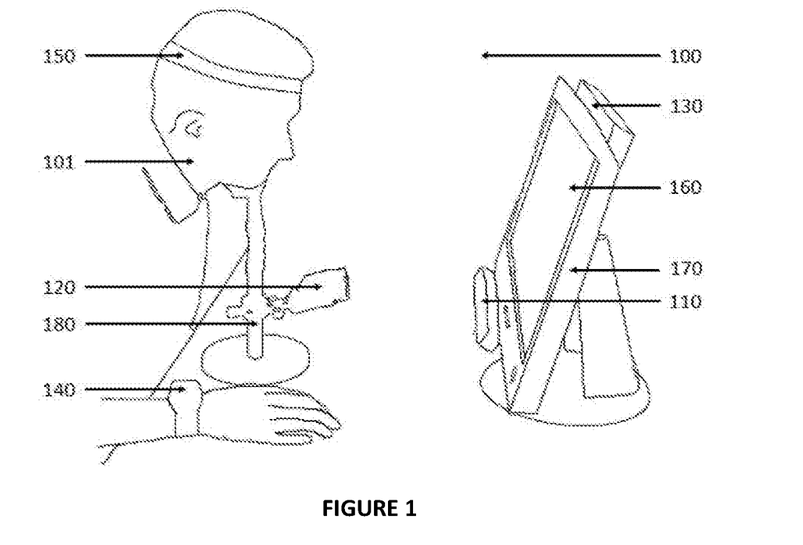
FIG. 1 shows a preferred embodiment of the physiological response measurement system according to an embodiment of the present invention.

FIG. 1 shows a preferred embodiment of the measurement system for a user's physiological responses according to an embodiment of the present invention. In this preferred embodiment of the invention, the physiological response measurement system 100 for a user, caused by cognitive load and stress, also comprises a chin support 180 in which the user 101 rests the chin, so that his face faces the eye measurement module 110.

In one embodiment, the eye measurement module 110 comprises infrared LEDs that emit radiation to track the relative position of the user's gaze on the screen, using the cornea's reflection detected with a video camera by means of mathematical geometric analysis models. This configuration of the ocular measurement module 110 allows measuring the Cartesian coordinates of the user's gaze in relation to the stimuli generated by the interaction and information presentation module 160. The detected coordinates are related to a time register measuring different variables for time, focus location on a photo, or other elements of interest.

Additionally, the ocular measurement module 110 is configured to detect changes in pupil dilation, that is, changes in pupil diameter, and determine the flicker frequency. These three variables correlate directly with the stress and cognitive load to which a user is subjected. Preferably, the eye measurement module camera 110 captures one hundred or more frames per second. According to a preferred embodiment, the eye measurement module 110 is fixed to the interaction and information presentation module 160 and placed in front of the user's face 101, to allow better system portability and obtain a field of vision centered on the user's eyes. In one embodiment of the invention, the eye measurement module 110 is configured to detect only the user's right eye. In another embodiment of the invention, the eye measurement module 110 is configured to detect only the user's left eye. Preferably, the eye measurement module 110 is configured to detect both of the user's eyes.

Preferably, the thermal measurement module 120 is fixed to the chin holder 180 to allow the thermal measurement module's 120 orientation towards the user's nostrils 101. This allows the infrared camera's field of vision to capture a greater amount of pixels with temperature changes caused by the flow of hot air from the user's exhalation. Joining the thermal measurement module 120 to the chin holder 180 thus provides better accuracy for detecting temperature changes, and allows a more accurate calculation of the user's respiratory rate. In one embodiment, the chamber of the thermal measurement module 120 is also configured to measure skin temperature on the user's face. More specifically, the camera is configured to detect temperature changes in three areas marked by a polygon. Preferably, the thermal measurement module 120 comprises wireless communication circuitry.

The facial measurement module 130 is configured to detect micro movements in the user's face that correlate with sustained stress. The facial measurement module 130 comprises a camera that detects changes in the position of reference points on the user's face. According to one embodiment of the invention, the camera is configured to detect information of at least twenty facial points, and preferably twenty-six points on the face. In another embodiment of the invention, the facial measurement module's camera 130 is fixed to the interaction and information presentation module 160 and placed in front of the user's face 101, to allow better system portability and obtain a field of view centered on the user face.

Figure 2:
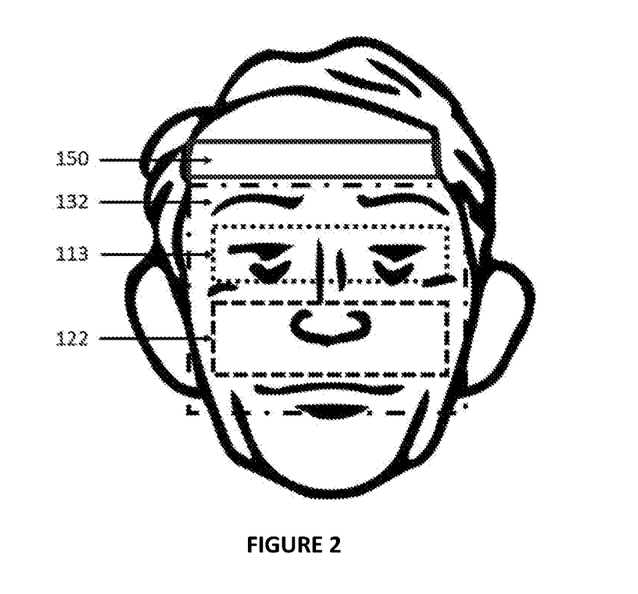
FIG. 2 shows examples of possible focus areas on the user's face by the physiological response measurement system according to an embodiment of the present invention.

FIG. 2 shows examples of possible areas of focus on the user's face by the physiological response measurement system, according to an embodiment of the present invention.

The camera in the eye measurement module 110 substantially concentrates its field of vision on the eye zone 113. The infrared camera of the thermal measurement module 120 substantially concentrates its field of vision on the nasal area 122. The camera of the face measurement module 130 substantially concentrates its field of vision on the facial area 132.

The system comprises a sensor module 140 with sensors that are in contact with the user's skin. The sensor module 140 allows detection of the user's heart rate, skin conductivity, arm skin temperature and/or movement. Preferably, the sensor module 140 may be a wrist accessory. In one embodiment, the sensor module 140 comprises a photoplethysmography (PPG) sensor with a transmitter with a wavelength between 480 nm and 540 nm, which detects changes in the pulsated volume of blood to calculate the user's heart rate variation (HRV).

According to a preferred embodiment, the sensor module 140 further comprises a 3-axis accelerometer. Preferably, the sensor module 140 acquires skin conductivity data by means of at least two electrodes in direct contact with the user's skin. In one embodiment of the invention, the sensor module 140 comprises a thermopile to detect the user's skin temperature. More preferably, the thermopile of the sensor module 140 is an infrared thermopile.

In a preferred embodiment, the sensor module 140 is configured to measure skin conductivity, heart rate, arm skin temperature and 3-axis movement information, where all the information is referenced to a time record. Preferably, the sensor module 140 comprises wireless communication circuitry.

In a preferred embodiment of the invention, the user's arm temperature information detected by the sensor module 140 and the face temperature information detected by the infrared camera 121 of the thermal measurement module 120, are used jointly to improve detection of changes in the user's temperature. In a preferred embodiment, the temperature information of the user's arm detected by the sensor module 140 is deemed a base body temperature with fewer variations, and is used as the basis for comparing temperature changes detected in the user's face skin by the infrared camera of the thermal measurement module 120.

The electroencephalography signals describe the user's brain activity by measuring the electrical potentials of the brain and allow an estimation of the user's cognitive load at a specific time. The system comprises an electroencephalography (EEG) 150 signal capture module that can be located at the top of the user's head as shown in FIG. 1. The module may include a helmet band or element. Additionally, the electroencephalography (EEG) 150 signal capture module preferably comprises at least four electrodes.

The interaction and presentation module 160 allows providing different types of stimuli to the user. The stimuli can be visual text, images without text or auditory type. A text-like visual stimulus can be a question or a mathematical operation presented in the form of text. An image without text can be a photo of an object or a person of interest. The auditory stimuli can be noises, questions, mathematical operations or verbal sentences.

The interaction and information presentation module 160 is also configured to receive user responses to the stimuli presented. In one embodiment of the invention, responses can be received in a pulsed manner. In another embodiment of the invention, responses can be received verbally. Preferably, the interaction and information presentation module 160 comprises peripherals selected from the group including: a digital display, headphones, a microphone, a mouse and a keyboard.

In another embodiment of the invention, the information interaction and presentation module 160 comprises a digital touch screen that allows the user to respond directly to the stimulus presented to him or her. In one embodiment of the invention, the interaction and information presentation module 160 is configured to measure the user's response time to the stimulus.

Figure 3:
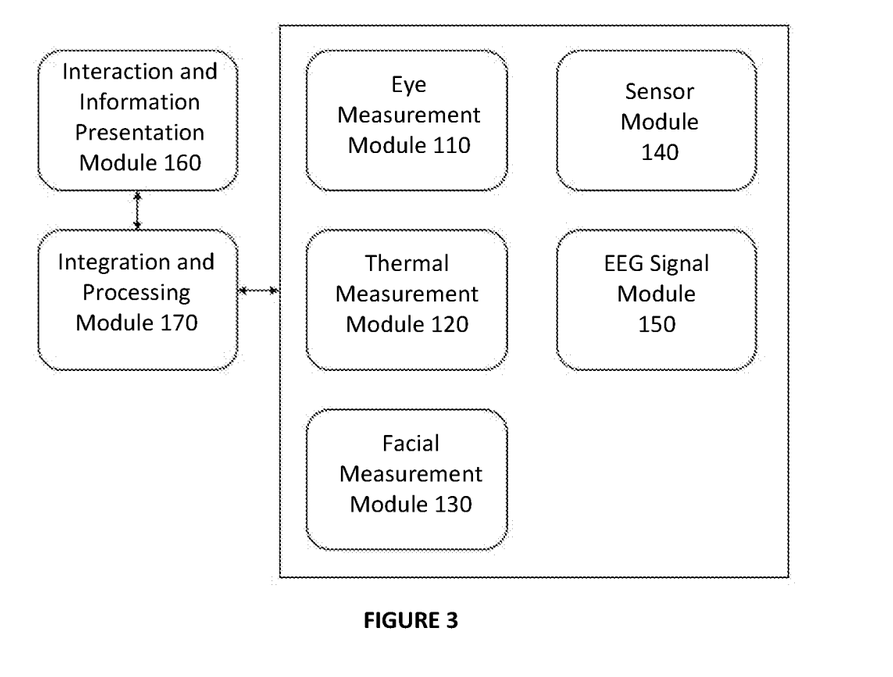
FIG. 3 shows a schematic diagram of the physiological response measurement system modules according to an embodiment of the present invention.

FIG. 3 shows a schematic diagram of the physiological response measurement system modules according to an embodiment of the present invention. The integration and processing module 170 is configured to receive signals from the eye measurement module 110, the thermal measurement module 120, the facial measurement module 130, the sensor module 140 and the EEG signal capture module 150. Additionally, it is configured to receive information on the stimuli presented and the responses entered in the interaction and information presentation module 160. According to one embodiment, the integration and processing module 170 comprises wireless communication circuitry. Preferably, the integration and processing module 170 is configured to receive information simultaneously from the other modules.

In a preferred embodiment of the invention, the integration and processing module 170 is configured to determine the level of cognitive load and stress by relating the user's responses to the stimuli presented by the interaction and information presentation module 160 by means of an algorithm, selected from the group consisting of: neural network, logistic regression, gradient tree boosting (GTB), random forests or dichotomous algorithm.

In one embodiment, the integration and processing module 170 is configured to prepare the data so that the different data from each sensor are aligned by their time register. Additionally, the module is configured to perform a precalculation for each combination of sensor, question topic and type of question, where each combination has a different preparation equation.

Each preparation equation may have factors that result from the experimental review of the data, for example: Elimination of 0, average value of the channel in that type/topic question. In certain cases it may include a time window. For example, after the response, ignoring the data before the user's response.

According to a preferred embodiment, the integration and processing module 170 is configured to discard channels or assign priorities and greater preference to specific variables received when determining the level of cognitive load and stress related to user responses.

In one embodiment of the invention, the integration and processing module 170 is configured to classify the results on the basis of several or all of the algorithms, and present the performance of each after a cross-validation using a Receiver Operating Characteristic curve (ROC), and a confusion matrix.

In a preferred embodiment of the invention, the information interaction and presentation module 160 is a personal computer. According to another embodiment of the invention, the integration and processing module 170 is also a computer. Preferably, the interaction and presentation modules 160 and integration and processing modules 170 are integrated into the same computer. In another embodiment, the interaction and presentation modules 160 and integration and processing modules 170 are integrated into a tablet device.

Figure 4:
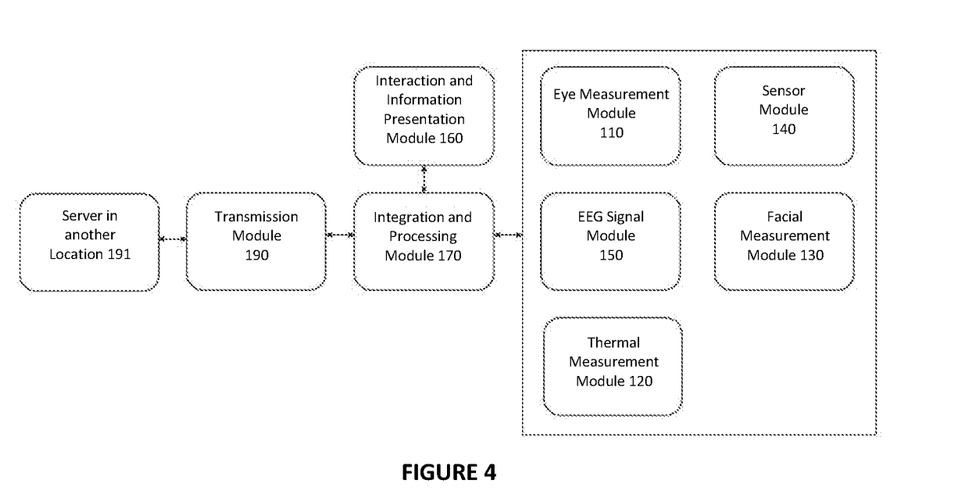
FIG. 4 shows a schematic diagram of the physiological response measurement system modules according to another embodiment of the present invention.

FIG. 4 shows a schematic diagram of the modules in the physiological response measurement system, according to another embodiment of the present invention. In said embodiment, the system also comprises a transmission module 190 that transmits the information collected to a server at another location 191. Optionally, the server at another location 191 is configured to determine the level of cognitive load and stress based on an algorithm selected from the group consisting of: neural network, logistic regression, gradient tree boosting (GTB), random forests or dichotomous algorithm. According to a preferred embodiment of the invention, the transmission module 190 is integrated into the same computer as the interaction and presentation modules 160 and integration and processing modules 170.

According to a preferred embodiment, the server in another location 191 is configured to discard channels or assign priorities and greater preference to specific variables received when determining the level of cognitive load and stress related to user responses.

In one embodiment of the invention, the server at another location 191 is configured to classify the results on the basis of several or all of the algorithms and present the performance of each after a cross-validation using a Receiver Operating Characteristic curve (ROC) and a confusion matrix.

Figure 5:
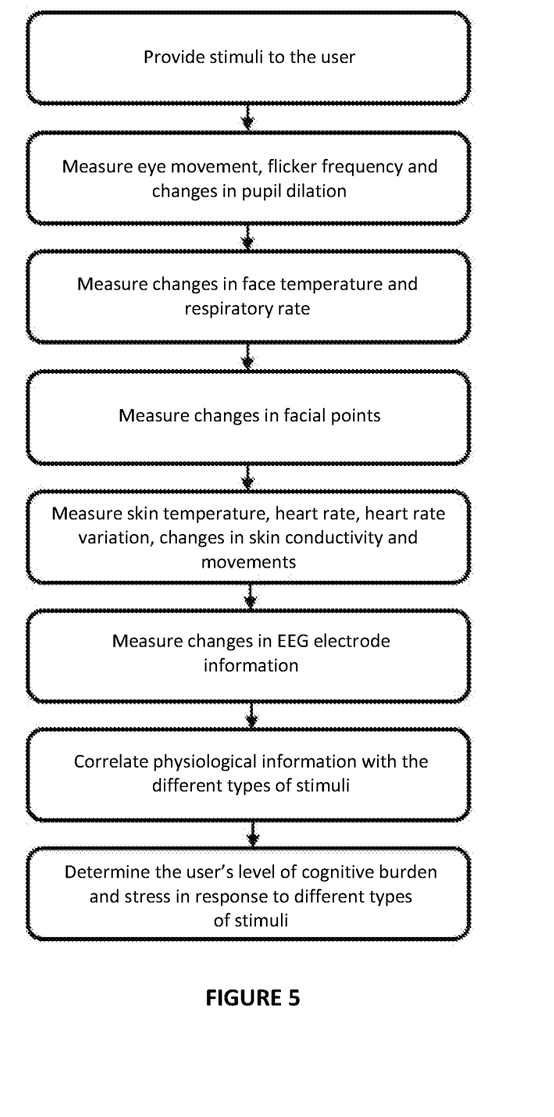
FIG. 5 shows a flow chart for the physiological response measuring method, according to an embodiment of the present invention.

Another aspect of the invention relates to methods of measuring physiological responses caused by cognitive load and stress. FIG. 5 shows a flow chart of the method for measuring physiological responses according to an embodiment of the present invention, which includes the steps of: a) providing stimuli to the user in an interaction and information presentation module 160, wherein the user stimuli can be visual text, image(s) without text, auditory, or combinations thereof; b) measuring eye movement, flicker frequency and changes in pupil dilation by means of a video camera; c) measuring changes in a user's face temperature and respiratory rate by means of an infrared camera; d) measuring changes in the user's facial points by means of a second video camera; e) measuring skin temperature, heart rate, heart rate variation, changes in skin conductivity and/or movements of the user's hand through a sensor module in direct contact with the skin; f) measuring changes in electroencephalography electrode (EEG) information; g) correlating the physiological information obtained in the previous steps with the different types of stimuli provided; and h)

determining the user's level of cognitive load and stress in response to the different types of stimulus to calculate a probability of deception in his or her conscious responses.

In one embodiment of the invention, step a) provides stimuli of different types such as text-type visuals, image without text type, auditory type or combinations thereof; and on different subjects, where the subjects may be relevant topics, relevant topics on which there is a certainty of honesty, relevant issues where instructions to lie are given, or neutral issues that exert cognitive load such as mathematical operations or riddles.

According to an embodiment of the invention, the information interaction and presentation module 160 is configured to show another stimulus in three different configurations. The interaction and information presentation module 160 can show another stimulus when the user actively responds to a stimulus, only when a certain time passes or when a certain time goes by if there is no response.

In one embodiment, the method may include a data preparation stage where the different data from each sensor are aligned by their time register. Additionally, this stage may contain a pre-calculation for each sensor combination, question topic and type of question, where each combination has a different preparation equation.

Each preparation equation may have factors resulting from experimental review of the data, for example: Elimination of 0, average value of the channel in that type/topic question. In certain cases it may include a time window. For example, after the response, ignoring the data before the user's response. Preferably, step g) is performed in the integration and processing module 170 and is configured to receive the information from the other modules simultaneously.

In one embodiment of the present invention, step h) is carried out in the integration and processing module 170, when configured to determine the level of cognitive load and stress by relating the user's responses to the stimuli presented by the interaction and presentation of information module 160, by means of an algorithm selected from the group consisting of: neural network, logistic regression, gradient tree boosting (GTB), random forests or dichotomous algorithm.

In one embodiment of the invention, the integration and processing module 170 can classify the results on the basis of several or all algorithms and present the performance of each after a cross-validation using a Receiver Operating Characteristic (ROC) curve and a confusion matrix.

According to a preferred embodiment, the integration and processing module 170 can discard channels or assign priorities and greater preference to specific variables received when determining the level of cognitive load and stress related to user responses.

Figure 6:
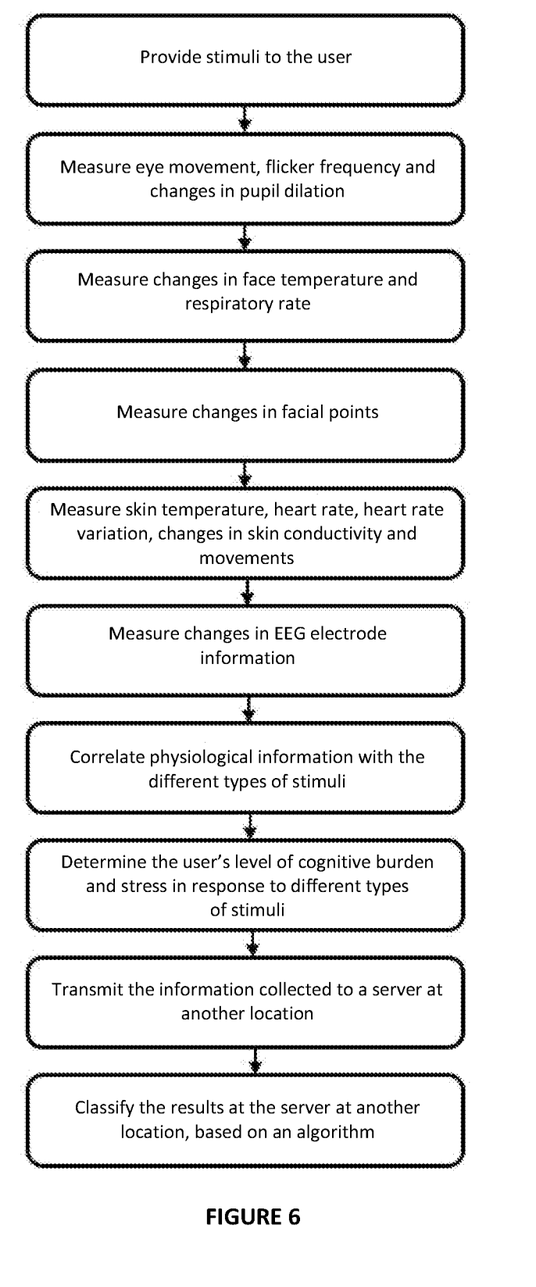
FIG. 6 shows a flow chart for the physiological response measuring method, according to another embodiment of the present invention.

FIG. 6 shows a flow chart for the physiological response measuring method, according to another embodiment of the present invention. In this preferred embodiment of the invention, the Claim's method of measuring a user's physiological responses caused by cognitive burden and stress also comprises i) transmitting the collected information to a server at another location 191 for processing. It may also comprise the step of j) classifying, on the server in another location 191, the results based on an algorithm selected from the group consisting of: neural network, logistic regression, gradient tree boosting (GTB), random forests or dichotomous algorithm. In one embodiment of the invention, the server at another location 191 can classify the results on the basis of several or all algorithms and present the performance of each after a cross-validation using a Receiver Operating Characteristic curve (ROC) and a confusion matrix.

According to a preferred embodiment, the server in another location 191 can discard channels or assign priorities and greater preference to specific variables received when determining the level of cognitive load and stress related to user responses.

The embodiments disclosed herein exemplify the invention, which is not limited to said embodiments, and its scope may include obvious variations and modifications of said embodiments.

Example 1

The system of the present invention can combine different types of stimuli and prioritize different changes in physiological variables. For example, the system can combine five different types of conditions:

| STIMULI | | PRIORITIZED VARIABLES |
|---|---|---|
| TYPE 1 | text visuals and auditory | Changes in pupil dilation, flicker frequency, pupil eye trajectory, face temperature and position of facial points. |
| TYPE 2 | text visuals and auditory | Changes in skin conductivity, heart rate, arm temperature, arm movements, electroencephalography signs, pupil dilation, flicker frequency, pupil eye trajectory, face temperature and facial points position. |
| TYPE 3 | image without text and auditory | Changes in pupil dilation, flicker frequency, pupil eye trajectory, face temperature and position of facial points. |
| TYPE 4 | auditory | Changes in skin conductivity, heart rate, arm temperature, arm movements, electroencephalography signs, pupil dilation, flicker frequency, pupil eye trajectory, face temperature and facial points position. |
| TYPE 5 | image without text | Changes in skin conductivity, heart rate, arm temperature, arm movements, electroencephalography signs, pupil dilation, flicker frequency, pupil eye trajectory, face temperature and facial points position. |

The invention claimed is:

1. A system for measuring physiological responses caused by cognitive load and stress, characterized in that it comprises:
   an eye measurement module containing a video camera and infrared LEDs focused on a user's pupils, where the eye measurement module is configured to:
   determine changes in pupil dilation,
   determine the blink rate, and
   determine the pupil's eye trajectory;
   a thermal measurement module containing an infrared camera arranged to measure changes in a user's face temperature and respiratory rate;
   a facial measurement module containing a camera that detects changes of position in at least twenty facial points of a user;
   a sensor module that includes sensors selected from the group comprising: heart rate sensors, skin conductivity sensors, motion sensors, and temperature sensors;
   an electroencephalography signal (EEG) capture module;
   an interaction and information presentation module configured to provide at least one stimulus to the user and record a conscious response from the user;
   wherein the at least one stimulus can be visual or auditory; in the form of a question or an image, or combinations thereof, wherein in said question or image can be of different types;

an integration and processing module configured to:
receive signals simultaneously from the eye measurement module, the thermal measurement module, the facial measurement module, the sensor module and the EEG signal capture module and convert said signals to data,
align the data to a data time register,
perform a pre-calculation utilizing the data for each combination of sensor and type of question or image, where each combination has a different preparation equation,
determine the level of cognitive load and stress based on an algorithm selected from the group consisting of: gradient tree boosting (GTB), and random forests;
discard data or assign priorities to specific data;
transmit the data to a server at another location for processing;
classify on the server in another location, the results based on the algorithm and present the performance of the algorithm; and cross-validate the algorithm using a Receiver Operating Characteristic curve (ROC) and a confusion matrix;
wherein the system determines changes in the user's physiological variables associated with stress and cognitive load in response to the stimulus generated by the interaction and information presentation module, to calculate a probability of deception in conscious responses.

2. The measurement system for physiological responses caused by cognitive load and stress of claim 1, characterized in that it also includes a chin support in which the user rests his or her chin and so faces the eye measurement module.

3. The measurement system for physiological responses caused by cognitive load and stress of claim 2, characterized in that the thermal measurement module is fixed to the chin holder.

4. The measurement system for a user's physiological responses caused by cognitive load and stress of claim 1, characterized in that the electroencephalography (EEG) signal capture module comprises at least four electrodes.

5. The measurement system for physiological responses caused by cognitive load and stress of claim 1, characterized in that the ocular measurement module is fixed to the interaction and information presentation module and sits in front of the user's face.

6. The measurement system for physiological responses caused by cognitive load and stress of claim 4, characterized in that the camera of the ocular measurement module captures one hundred or more frames per second.

7. The measurement system for physiological responses caused by cognitive load and stress of claim 1, characterized in that the interaction and information presentation module comprises a digital touch screen.

8. The measurement system for physiological responses caused by cognitive load and stress of claim 1, characterized in that the sensor module comprises a photoplethysmography sensor (PPG) with a transmitter with a wave length between 480 nm and 540 nm that detects changes in the volume of pulsed blood to calculate the user's heart rate variation (HRV).

9. The measurement system for physiological responses caused by cognitive load and stress of claim 8, characterized in that the sensor module further comprises a 3-axis accelerometer.

10. The measurement system for physiological responses caused by cognitive load and stress of claim 1, characterized in that the sensor module is configured to obtain a first temperature information from the user, and the infrared camera of the thermal measurement module is configured to obtain a second temperature information from the user, wherein said first and second temperature information are used together to improve detection of user temperature changes.

11. The measurement system for physiological responses caused by cognitive load and stress of claim 1, characterized in that it further comprises a transmission module that transmits the information collected to a server at another location.

12. The measurement system for physiological responses caused by cognitive load and stress of claim 11, characterized in that the server at another location is configured to determine the level of cognitive load and stress based on an algorithm selected from the group consisting of: neural network, logistic regression, gradient tree boosting (GTB), and random forests.

13. A method of measuring physiological responses caused by cognitive load and stress, comprising:
a. providing stimuli to a user in an interaction and presentation module, wherein the stimuli to the user are selected from the group comprising: visual or auditory or combinations thereof; wherein in said question or image can be of different types;
b. measuring eye movement, flickering frequency and changes in pupil dilation through a video camera;
c. measuring changes in a user's face temperature and respiratory rate using an infrared camera;
d. measuring changes in at least twenty facial points of the user by means of a second video camera;
e. measuring skin temperature, heart rate, heart rate variation, changes in skin conductivity and movements of the user's hand by means of a sensor module in direct contact with the skin;
f. measuring changes in electroencephalography (EEG) electrode information;
wherein measurements collected in steps b through f are converted in to data
aligning the data to a sensor time register,
g. correlating the data with the different types of stimuli provided,
performing a pre-calculation utilizing the data for each combination of sensor, and type of question or image, where each combination has a different preparation equation;
h. determining the user's level of cognitive load and stress in response to the stimuli by means of an algorithm selected from the group consisting of: gradient tree boosting (GTB), and random forests to calculate a probability of deception in conscious responses
discarding data or assigning priorities to specific data
i. transmitting the collected information to a server at another location for processing
j. classifying on the server in another location, the results based on the algorithm and present the performance of the algorithm after a cross-validation using a Receiver Operating Characteristic curve (ROC) and a confusion matrix.

14. The method of measuring physiological responses caused by cognitive load and stress of claim 13, characterized in that the stimuli are selected from the group consisting of: stimuli relevant to the subject of interest, comparative stimuli not relevant to the test, and neutral stimuli.

15. The method of measuring physiological responses caused by cognitive load and stress of claim 13, characterized in that it further comprises:

i. transmitting the information collected to a server at another location for processing.

* * * * *